United States Patent [19]

Asato

[11] 4,153,611
[45] May 8, 1979

[54] SUBSTITUTED TETRAHYDROBENZOTHIOPHENES AND METHOD OF PREPARATION THEREOF

[75] Inventor: Goro Asato, Titusville, N.J.

[73] Assignee: American Cyanamid Company, Stamford, Conn.

[21] Appl. No.: 912,811

[22] Filed: Jun. 5, 1978

Related U.S. Application Data

[63] Continuation of Ser. No. 684,700, May 10, 1976, abandoned, which is a continuation-in-part of Ser. No. 532,449, Dec. 13, 1974, abandoned, which is a continuation-in-part of Ser. No. 436,827, Jan. 25, 1974, abandoned.

[51] Int. Cl.$^2$ ..................... C07D 333/16; A01N 9/00
[52] U.S. Cl. ......................... 260/332.3 P; 260/329 F; 260/329 S; 260/329 HS; 260/329 AM; 260/332.2 A; 260/332.3 C; 260/332.5; 424/275; 426/648
[58] Field of Search ..... 260/329 S, 329 HS, 329 AM, 260/329 F, 332.2 A, 332.3 C, 332.3 P, 332.5

[56] References Cited

U.S. PATENT DOCUMENTS 3,998,959   12/1976   Asato et al. ................... 260/332.2 R Primary Examiner—A. Siegel
Attorney, Agent, or Firm—Harry H. Kline

[57] ABSTRACT

This disclosure describes novel 5,6,7,8-tetrahydro-4$\underline{H}$-cyclohepta[b]thien-4-ylureas useful as animal growth regulants and processes for the preparation thereof.

22 Claims, No Drawings

SUBSTITUTED TETRAHYDROBENZOTHIOPHENES AND METHOD OF PREPARATION THEREOF

CROSS REFERENCE TO RELATED APPLICATIONS

This application is a continuation of my copending application, Ser. No. 684,700, filed May 10, 1976 now abandoned, which is a continuation-in-part of my abandoned application Ser. No. 532,449, filed Dec. 13, 1974, which in turn is a continuation-in-part of my abandoned application, Ser. No. 436,827, filed Jan. 25, 1974.

BRIEF SUMMARY OF THE INVENTION

This invention relates to novel 5,6,7,8-tetrahydro-4H-cyclohepta[b]thien-4-ylureas which may be represented by the following general formula:

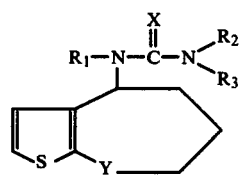

(I)

wherein X is divalent oxygen or divalent sulfur; Y is a divalent moiety of the formulae:

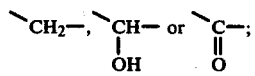

$R_1$ is hydrogen or alkyl $C_1$–$C_4$; $R_3$ is hydrogen, alkyl $C_1$–$C_4$, cycloalkyl $C_3$–$C_6$, allyl, 2-propynyl, benzyl or β-phenylethyl; $R_2$ is selected from the group consisting of the substituents listed in Table I below:

TABLE I

| $R_2$ |
| --- |
| hydrogen |
| alkyl $C_1$–$C_{12}$ |
| cycloalkyl $C_3$–$C_6$ |
| allyl |
| methallyl |
| 2-butenyl |
| 2-propynyl |
| hydroxy |
| alkoxy $C_1$–$C_6$ |
| allyloxy |
| methallyloxy |
| 2-butenyloxy |
| methoxymethyl |
| —O—CH$_2$—COOH |
| phenoxy |
| benzyloxy |
| —CH$_2$—CH$_2$—OH |
| —CH$_2$—CH$_2$—O—CH$_3$ |
| —CH$_2$—CH$_2$—S—CH$_3$ |
| —CH$_2$—CH(OR)$_2$ |
| —CH$_2$—CF$_3$ |
| —CH$_2$—CN |
| —CH$_2$—CO$_2$R |
| —NH—CO$_2$R |
| $-\overset{\overset{O}{\|}}{C}-R$ |
| $-\overset{\overset{O}{\|}}{C}-CCl_3$ |

TABLE I-continued

| $R_2$ |
| --- |

(structures shown: tetrahydronaphthyl; furfuryl (O-CH$_2$—); furan-carboxamide (O-C(=O)-NH—); thienylmethyl (S-CH$_2$—); 4-methyltetrahydrobenzothienyl; tetrahydrobenzothienyl-NH-C(=O)-NH-CH$_2$—; pyridyl-CH$_2$—; pyridyl-CH$_2$—CH$_2$—; Q-phenyl-(CH$_2$)$_n$—)

wherein (in Table I) R is alkyl $C_1$–$C_4$, n is 0, 1 or 2, and Q is selected from the group consisting of the substituents listed in Table II below:

TABLE II

| | Q | |
| --- | --- | --- |
| n = 0 | n = 1 | n = 2 |
| 2-methyl-4-bromo | hydrogen | hydrogen |
| 3,4-methylenedioxy | 4-chloro | |
| 3- or 4-methoxy | 4-methoxy | |
| 4-ethoxy | 3,4-methyl- | |
| 4-chloro | enedioxy | |
| 4-butoxy | | |
| 4-methylthio | | |
| 2,4-dimethyl | | |
| 2,5-dimethoxy | | |
| 2,4-dichloro | | |
| 4-nitro | | | and $R_2$ and $R_3$ taken together with the associated N(itrogen) is selected from the group consisting of morpholino, piperidino, pyrrolidino, 4-phenylpiperazino, 4-(4-methoxyphenyl)piperazino, 4-carbethoxypiperazino, 4-oxopiperazino, 1,2,3,4-tetrahydroquinolino and the moiety of the formula:

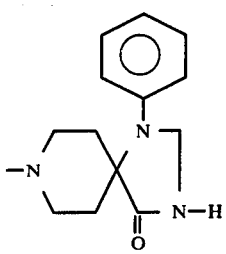

DETAILED DESCRIPTION OF THE INVENTION

A preferred embodiment within the scope of the present invention may be represented by the following formula:

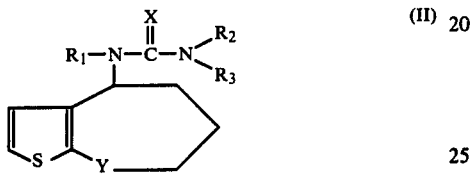

(II)

wherein X, Y, $R_1$ and $R_3$ are as hereinabove defined and $R_2$ is selected from the group consisting of the substituents listed in Table III below:

Table III

| $R_2$ |
| --- |
| hydrogen |
| alkyl $C_1$-$C_8$ |
| cycloalkyl $C_3$-$C_6$ |
| allyl |
| methallyl |
| 2-butenyl |
| 2-propynyl |
| hydroxy |
| alkoxy $C_1$-$C_6$ |
| allyloxy |
| methallyloxy |
| 2-butenyloxy |
| methoxymethyl |
| phenoxy |
| —$CH_2$—$CH_2$—OH |
| —O—$CH_2$—COOH |
| —$CH_2$—CH(OR)$_2$ |
| —$CH_2$—$CF_3$ |
| —$CH_2$—CN |
| —NH—$CO_2$R |
| $\overset{O}{\underset{\|}{-C}}$—R |
| $\overset{O}{\underset{\|}{-C}}$—$CCl_3$ |
| 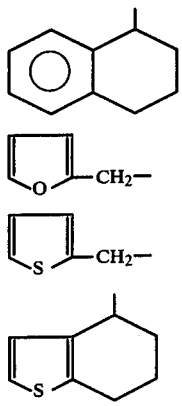 |

Table III-continued

| $R_2$ |
| --- |
| 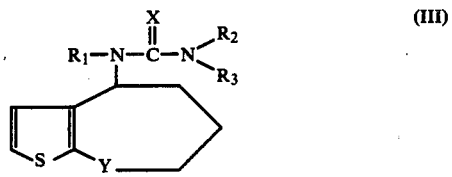 benzyloxy | wherein (in Table III) R and n are as hereinabove defined and Q is selected from the group consisting of the substituents listed in Table IV below:

TABLE IV

| Q | | |
| --- | --- | --- |
| n = 0 | n = 1 | n = 2 |
| 4-chloro | hydrogen | hydrogen |
| 3,4-methylene-dioxy | 4-methoxy | |
| 3- or 4-methoxy | | |
| 4-ethoxy | | |
| 4-butoxy | | |
| 4-methylthio | | |
| 2,4-dimethyl | | |
| 2,4-dichloro | | |
| 4-nitro | | |
| 2-methyl-4-bromo | | |

Another preferred embodiment within the scope of the present invention may be represented by the following formula:

(III)

wherein X, Y, $R_1$ and $R_3$ are as hereinabove defined and $R_2$ is selected from the group consisting of the substituents listed in Table V below:

TABLE V

| $R_2$ |
| --- |
| hydrogen |
| alkyl $C_1$-$C_8$ |
| cycloalkyl $C_3$-$C_4$ |
| allyl |
| 2-propynyl |
| hydroxy |
| alkoxy $C_1$-$C_6$ |
| methoxymethyl |
| phenoxy |
| 4-methoxyphenyl |
| 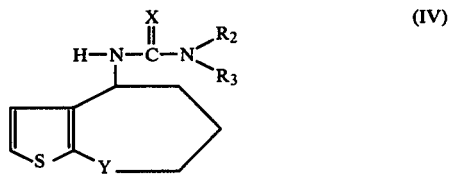 |

Another preferred embodiment within the scope of the present invention may be represented by the following formula:

(IV)

wherein X is as hereinabove defined and $R_2$ and $R_3$ taken together with the associated N(itrogen) is selected from the group consisting of morpholino, pyrrolidino, 4-phenylpiperazino, 4-(4-methoxyphenyl)piperazino, 1,2,3,4-tetrahydroquinolino and the moiety of the formula:

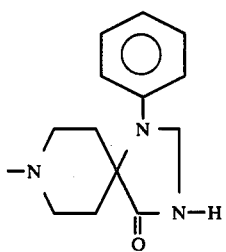

Another preferred embodiment within the scope of the present invention may be represented by the following formula:

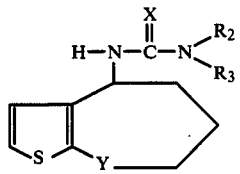

wherein X and Y are as hereinabove defined, $R_2$ is hydrogen, alkyl $C_1$-$C_8$, allyl, alkoxy $C_1$-$C_4$, 2-propynyl, methoxymethyl or hydroxy and $R_3$ is hydrogen or alkyl $C_1$-$C_4$.

A most preferred embodiment within the scope of the present invention may be represented by the following formula:

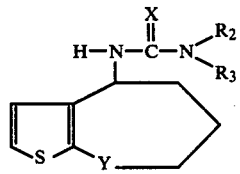

wherein X and Y are as hereinabove defined, $R_2$ is hydrogen or alkyl $C_1$-$C_4$ and $R_3$ is hydrogen or methyl.

Some of the novel compounds of the present invention (VI) may be readily prepared by reacting an appropriately substituted 5,6,7,8-tetrahydro-4H-cyclohepta[b]thiophen-4-amine (VII) with an appropriately substituted isocyanate or isothiocyanate (VIII) as set forth in the following reaction scheme:

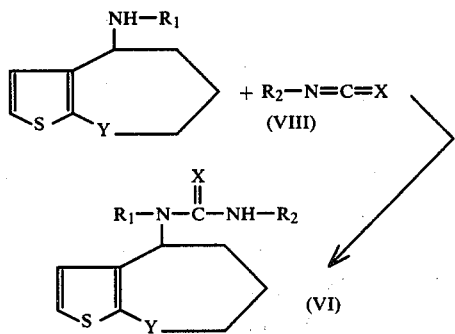

wherein X, Y, $R_1$ and $R_2$ are as hereinabove defined. The reaction can be carried out using approximately equimolar amounts of the isocyanate or isothiocyanate and the amine or amine acid salt; however, it is generally preferable to employ from 5% to 50% excess of the isocyanate or isothiocyanate wherein the tetrahydro-4H-cyclohepta ring does not contain a hydroxyl group. The reaction can be conducted at atmospheric or superatmospheric pressure at a temperature in the range of 0° to 100° C., but is preferably conducted at atmospheric pressure at 0° C. to 70° C. in the presence of an organic solvent. Suitable organic solvents include aprotic aromatic solvents such as benzene, toluene, and xylene; chlorinated hydrocarbon solvents such as methylene chloride, chloroform and dichloroethane; ethers such as tetrahydrofuran, diethyl ether, dimethoxyethane, diethylene glycol dimethyl ether, and dioxane; lower alkyl $C_1$-$C_4$ ketones such as acetone, methyl ethyl ketone, methyl butyl ketone and methyl isobutyl ketone, or mixtures of said solvents.

When the above reaction is carried out using a 5,6,7,8-tetrahydro-4H-cyclohepta[b]thiophen-4-amine acid salt, it is desirable to add an acid acceptor to the reaction mixture. Suitable acid acceptors include trialkylamines such as triethylamine, trimethylamine, pyridine or the like; alkali metal carbonates such as sodium and potassium carbonate; alkaline earth metal carbonates such as calcium carbonate; strong basic ion exchange resins; and aqueous alkali in a 2-phase system using an immiscible hydrocarbon solvent such as benzene or toluene, or a chlorinated hydrocarbon such as chloroform or dichloroethane.

Formula (I) 5,6,7,8-tetrahydro-4H-cyclohepta[b]thien-4-ylurea compound wherein $R_2$ and $R_4$ are hydrogen may be advantageously prepared from the above-identified amine (VII) or its acid salt by reacting said amine with an approximately equimolar amount of sodium or potassium cyanate or thiocyanate. However, it is generally preferable to employ 5% to 50% excess of the cyanate or thiocyanate wherein the tetrahydro-4H-cyclohepta ring does not contain a hydroxy group. The reaction can be conducted under the conditions described above in detail. Suitable solvents include water, polar solvents such as $C_1$-$C_3$ alcohols, tetrahydrofuran, dioxane, ethyleneglycol dimethyl ether, diethylene glycol, dimethyl ether, acetone, methyl ethyl ketone and the like and mixtures thereof; in the pH range of 5 to 7 and preferably at pH 6.

Certain of the formula (I) 5,6,7,8-tetrahydro-4H-cyclohepta[b]thien-4-ylurea compounds (XI) may be readily prepared by reacting approximately equimolar amounts of an appropriately substituted 5,6,7,8-tetrahydro-4H-cyclohepta[b]thien-4-yl isocyanate or isothiocyanate (IX) and an appropriately substituted $R_2R_3NH$ amine (X) or its acid-addition salt. The reaction can be graphically illustrated as follows:

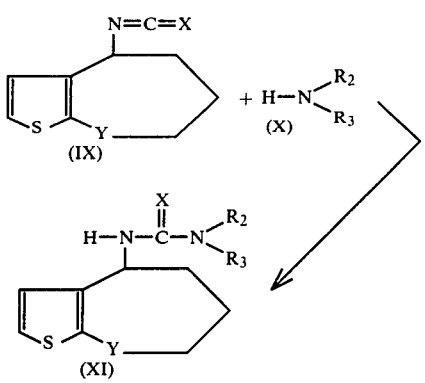

wherein X, Y, R$_2$ and R$_3$ are as hereinabove defined; with the proviso that Y is not —CHOH. In practice, the reaction is usually conducted with a slight excess (i.e. up to 20% excess) of the amine in the presence of a solvent, such as described above. Although the reaction may be conducted at superatmospheric pressure and temperatures as high as 100° C., it is generally preferable to conduct the reaction at atmospheric pressure at a temperature between 0° C. and 80° C. When a R$_2$R$_3$NH amine acid salt is used it is most beneficial to introduce into the reaction mixture an acid acceptor such as described above. When an aqueous or a C$_1$-C$_3$ alcoholic ammonia or amine solution is used in the above reaction sequence, then the formula (XI) compounds are obtained wherein R$_2$ and R$_3$ are as defined above.

Preparation of the isocyanate (IX) utilized in the above reaction is readily accomplished by reacting the appropriate 5,6,7,8-tetrahydro-4H-cyclohepta[b]thiophen-4-amines or their acid salts with phosgene, preferably under anhydrous conditions and under a blanket of inert gas such as nitrogen. The reaction is initially carried out at a temperature between about 0° C. to 40° C., preferably 10° C. to 20° C., and then heated to between about 50° C. and 100° C., and preferably to from 60° C. to 80° C. The reaction is usually also conducted in the presence of an organic solvent such as benzene, toluene or xylene. The isothiocyanates (IX) can be prepared by reacting the appropriate 5,6,7,8-tetrahydro-4H-cyclohepta[b]thiophen-4-amines with equimolar amounts of carbon disulfide, triethylamine, and a carbodiimide represented by the formula: G—N=C=N—G where G is cyclohexyl, cycloheptyl, alkyl C$_4$-C$_6$ or the like. This reaction is generally conducted in the presence of a solvent such as tetrahydrofuran or an ether such as diethyl ether, at a temperature between about −10° C. and +25° C. The product can be isolated by distillation or by dry-column chromatography. Alternatively, the formula (IX) isothiocyanates can be prepared by the reaction of 1,1'-thiocarbonyldiimidazole with 5,6,7,8-tetrahydro-4H-cyclohepta[b]thiophen-4-amines in the presence of chloroform at ambient temperature.

The reaction of thiocarbonyl diimidazole in the above-mentioned reaction may also lead to the isolation of 1-(1-imidazolyl)-3-(5,6,7,8-tetrahydro-4H-cyclohepta[b]thien-4-yl)thiourea. The analogous reaction also occurs when carbonyl diimidazole is used at room temperature and these reactions may be illustrated as follows:

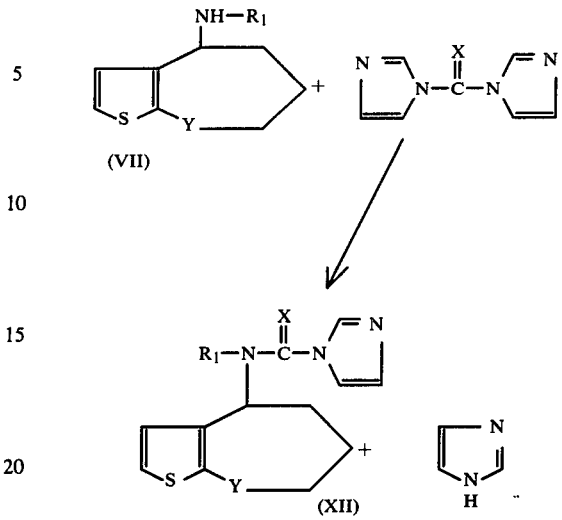

wherein R$_1$, Y, and X are as previously defined. This intermediate (XII) has been discovered to be useful for preparing growth promoting urea compounds especially when the corresponding 4-isocyanate or 4-isothiocyanates of the 5,6,7,8-tetrahydro-4H-cyclohepta[b]thiophen-4-amines are difficult to prepare by conventional methods. The reaction may be illustrated as follows:

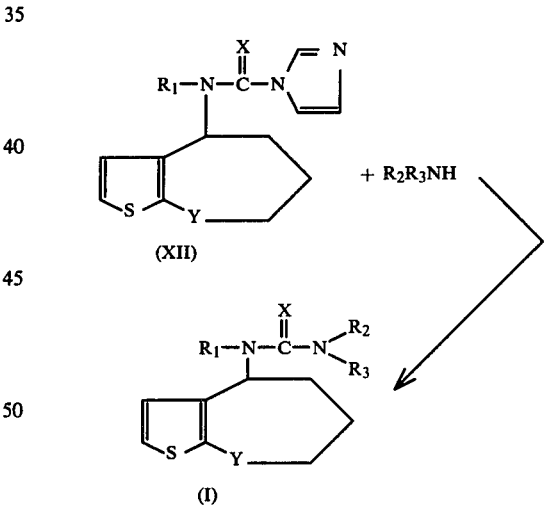

The reaction is run at room temperature to 100° C. and preferably at 25° C.-50° C. in inert solvents such as chloroform, tetrahydrofuran, methylene chloride and the like.

Advantageously, formula (I) 5,6,7,8-tetrahydro-4H-cyclohepta[b]thien-4-ylurea compounds wherein Y is carbonyl (XIV) may be readily prepared from the corresponding formula (I) compounds wherein Y is methylene (XIII) by an oxidation reaction as set forth in the following reaction scheme:

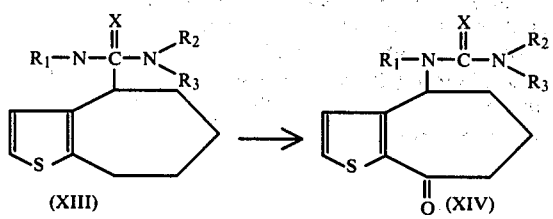

wherein X, $R_1$, $R_2$ and $R_3$ are as hereinabove defined with the proviso that $R_2$ cannot be hydroxyl, or a group containing hydroxyl, or —$SCH_3$, or an aryl-$CH_3$, or an aryl- or heteroaryl-methylene. The oxidation is carried out by treating a compound of formula (XIII) with a 2 to 8 mole equivalent and preferably with a 4 to 5 mole equivalent of an oxidizing agent selected from the group consisting of ceric ammonium nitrate, silver oxide, or sodium bichromate, at a temperature between about 0° C. and 100° C., and preferably 20° C. to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or the oxidizing agent chromic anhydride in acetic anhydride followed by hydrolysis.

Furthermore, formula (I) 5,6,7,8-tetrahydro-4H-cyclohepta[b]thien-4-ylurea compounds wherein Y is carbonyl (XVIII) can also be prepared by the above described oxidative process as set forth in the following reaction scheme:

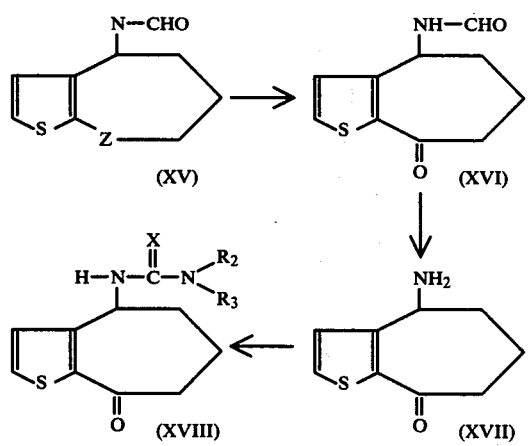

wherein Z is methylene or hydroxymethylene and X, and $R_2$ and $R_3$ are as hereinabove defined. Upon completion of the oxidation step, the resulting 8-oxo compounds (XVI) are hydrolyzed in dilute mineral acid. The thus obtained amine (XVII) acid-addition salts are then reacted with an isocyanate or an isothiocyanate at pH 5–7 as hereinbefore described in detail to yield the desired ureas or thioureas (XVIII).

The corresponding 8-hydroxy analogs are prepared from the corresponding formula (I) compounds wherein Y can be only carbonyl by reduction with equimolar or excess amounts of sodium borohydride, at a temperature range between about 0° C. and 75° C., preferably 20°–40° C., in $C_1$–$C_3$ alcohols to afford a mixture of the cis and trans isomers. All of the hereinabove described processes for the preparation of formula (I) 5,6,7,8-tetrahydro-4H-cyclohepta[b]thien-4-ylurea compounds yield racemic (dl) mixtures.

The novel compounds of the present invention may also be readily prepared by treating an appropriately substituted 5,6,7,8-tetrahydro-4H-cyclohepta[b]thiophen-4-amine (VII) with an appropriately substituted carbamoyl or thiocarbamoyl halide (XIX) as set forth in the following reaction scheme:

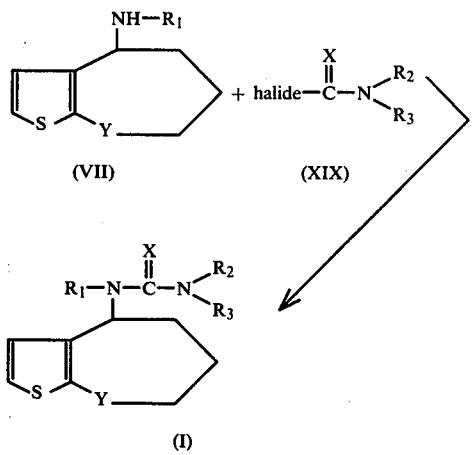

wherein $R_1$, $R_2$, $R_3$, X and Y are as hereinabove defined and halide may be chloro or bromo with the proviso that $R_2$ may not be hydroxyl, or a group containing hydroxyl, or a thioether. The free base of (VII) may be employed or an acid-addition salt thereof, preferably the hydrochloride, in the presence of an acid acceptor. Suitable acid acceptors may be pyridine, triethylamine (or any suitable tertiary amine), alkali metal carbonates such as potassium carbonate and sodium carbonate, strong basic ion-exchange resins, and aqueous alkali. The reaction may be run from about room temperature up to about 100° C. and preferably at 25°–50° C. until the desired reaction is complete. The reaction may be carried out under aqueous conditions or in any inert organic solvent such as tetrahydrofuran, dimethoxyethane, and even alcohols. The carbamoyl chloride or thiocarbamoyl chloride is generally used in equivalent amounts but it may be used in excess.

The preparation of the optically active 5,6,7,8-tetrahydro-4H-cyclohepta[b]thiophen-4-amine which is a useful intermediate for the synthesis of optically active 5,6,7,8-tetrahydro-4H-cyclohepta[b]thien-4-ylureas of formula (I) may be accomplished as follows. The racemic (dl) 5,6,7,8-tetrahydro-4H-cyclohepta[b]thiophen-4-amine is treated with the (+)-N-benzoylglutamic acid to form a water-insoluble salt of (+)-5,6,7,8-tetrahydro-4H-cyclohepta[b]thiophen-4amine in high yield. It is not necessary to employ more than one mole of the resolving acid for each two moles of dl amine as a cheaper acid, preferably acetic acid, can be substituted for the balance of required acid. In this way it is possible to obtain a high yield of the desired (+)-amine based on the resolving acid. The resolved salt, (+)-5,6,7,8-tetrahydro-4H-cyclohepta[b]thiophen-4-amine . (+)-N-benzoylglutamic acid, is treated with alkali which liberates the (+)-amine which separates as an insoluble phase. It can be mechanically separated from the aqueous phase or extracted conventionally with a suitable solvent.

The (−)-amine which remains in solution is then recovered and treated with (−)-N-benzoylglutamic acid and acetic acid in the above-mentioned manner with the molarity adjusted to the amount of (+) amine obtained from the initial resolution. The salt, (−)-5,6,7,8-tetrahydro-4H-cyclohepta[b]thiophen-4-amine . (−)-N-benzoylglutamic acid, crystallizes and is then treated in the above-mentioned manner to give the (−)-amine.

With respect to optical isomers, the most preferred optically active ureido compounds for enhancement of growth in animals are those which are derived from the (+)-5,6,7,8-tetrahydro-4H-cyclohepta[b]thiophen-4-amine. Thus, the following reaction schemes will exemplify the sequence in the preparation of the optically active compounds.

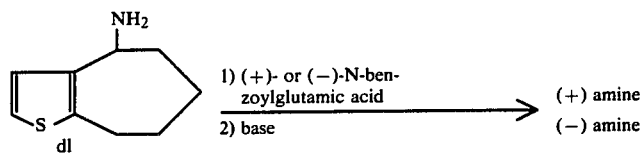

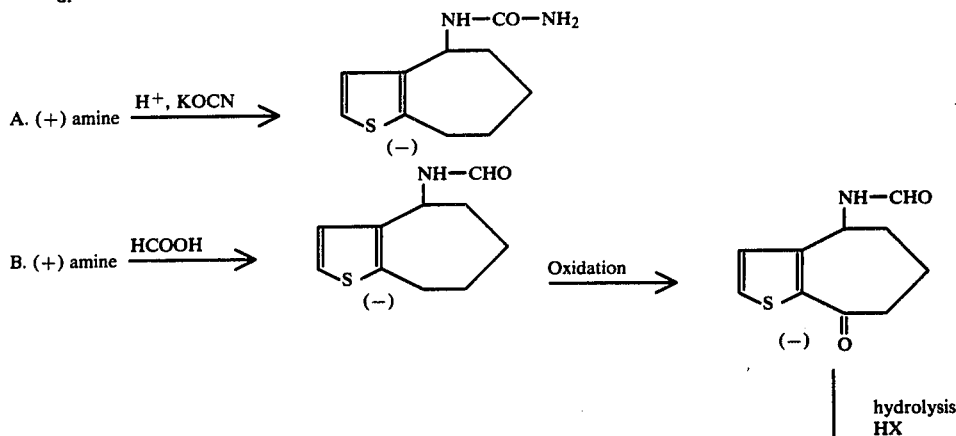

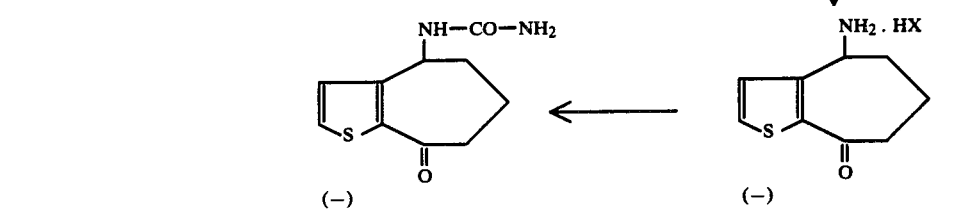

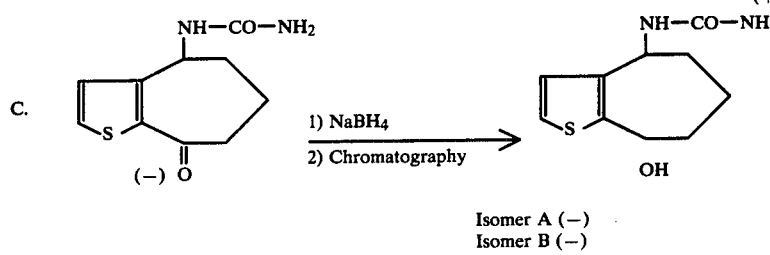

Isomer A (−)
Isomer B (−)

The separation of cis and trans-(−)-5,6,7,8-tetrahydro-7-hydroxy-4H-cyclohepta[b]thien-4-ylureas is readily achieved by using preparative high-pressure liquid chromatography on silica gel with 1800 ml. of hexane/1000 ml. of CHCl$_3$/425 ml. of MeOH at a flow-rate of 40 ml./minute. Since the configurations have not been established, the isomers are designated as Isomer A and Isomer B. Conversely, if (−)-5,6,7,8-tetrahydro-4H-cyclohepta[b]thiophen-4-amine is used in the above sequence, the resulting derivatives of the opposite sign are obtained.

Because 5,6,7,8-tetrahydro-7-oxo-4H-cyclohepta[b]-thiophen-4-amine is also a useful intermediate, this compound in its optically active form is desirable. Thus, dl-5,6,7,8-tetrahydro-7-oxo-4H-cyclohepta[b]thiophen-4-amine is readily resolved with (+)-tartaric acid in methanol as follows:

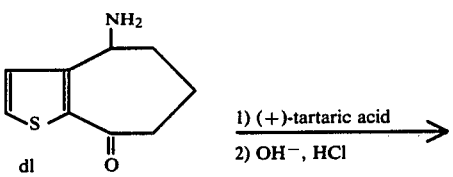

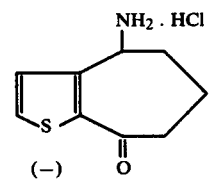

and the resulting crystalline tartrate salt is recrystallized from 95% ethanol. The salt is decomposed with aqueous NaOH solution and the optically active keto-amine is separated by conventional extraction and acidified with HCl to afford (−)-5,6,7,8-tetrahydro-7-oxo-4H-cyclohepta[b]thiophen-4-amine hydrochloride, which can be used in the manner described above.

The compounds of this invention are useful as growth-promoting agents for animals such as poultry, fur-bearing and farm animals, and the use of said compounds for this purpose provides the added advantage of improving feed conversion for said animals. As used herein, the term "feed conversion" means the ratio of unit weight of feed per unit weight of gain and improvement in feed conversion means increased weight gain from a given unit of feed consumed.

In practice, a growth-promoting amount of a formula (I) 5,6,7,8-tetrahydro-4-H-cyclohepta[b]thien-4-ylurea or an optically active isomer is administered to a host animal usually in, or with, the animal's feed. However, said compound may also be administered as a subcutaneous implant under the skin of said animal or as a parenteral injection. When administered in the feed of chickens, turkeys, sheep, cattle, goats, and the like, usually about 0.0001% to 0.08% by weight and preferably 0.001% to 0.04% by weight of the formula (I) urea, is effective for increasing growth rate and improving feed conversion. When administered to said animals as a parenteral injection or subcutaneous implant, usually in amounts that will supply about 0.001 mg. to 0.20 mg. and preferably 0.005 mg. to 0.10 mg. per kg. of body weight per day of the active compound, will produce the desired improvement in weight gain and enhance food conversion. In tests conducted with day old chicks, it was found that from 1 ppm to 9 ppm of 5,6,7,8-tetrahydro-4H-cyclohepta[b]thien-4-ylurea should be administered in the chick feed to produce the desired improvement in weight gain over untreated controls, and likewise to produce improvement in feed conversion.

The present invention is further illustrated by the preparation of representative examples set forth below, as well as testing data on typical compounds of the invention.

EXAMPLE 1

Preparation of 1-methyl-3-(5,6,7,8-tetrahydro-4H-cyclohepta[b]thien-4-yl)urea 5,6,7,8-Tetrahydro=4H-cyclohepta[b]thiophen-4-one is converted to N-(5,6,7,8-tetrahydro-4H-cyclohepta[b]thien-4-yl)formamide, m.p. 164°–166° C., by the method of Xloetzel et al., Journal of Organic Chemistry 18, 1511 (1953). Hydrolysis of the formanide is accomplished by refluxing for one hour in 1 N hydrochloric acid and evaporating to dryness to afford 5,6,7,8-tetrahydro-4H-cyclohepta[b]thiophen-4-amine hydrochloride, m.p. 233°–236° C. dec. The amine hydrochloride is then allowed to react with methyl isocyanate in dry tetrahydrofuran as solvent in the presence of a stoichiometric equivalent of triethylamine to afford 1-methyl-3-(5,6,7,8-tetrahydro-4H-cyclohepta[b]thien-4-yl)urea, m.p. 220°–222° C.

Similarly, by substituting ethyl isothiocyanate for methyl isocyanate in the above procedure there is obtained 1-ethyl-3-(5,6,7,8-tetrahydro-4H-cyclohepta[b]-thien-4-yl)-2-thiourea, m.p. 117°–120° C.

EXAMPLE 2

Preparation of 5,6,7,8-tetrahydro-4H-cyclohepta[b]thien-4-ylurea

A mixture of 50 grams of 5,6,7,8-tetrahydro-4H-cyclohepta[b]thiophen-4-amine hydrochloride in 100 ml. of water is stirred at about 15° C. and a solution of 23.1 grams of potassium cyanate in 100 ml. of water is added dropwise. After completion of the addition, the mixture is warmed slowly to 70°–75° C. and held there for one hour. The mixture is cooled and the white solid is collected by filtration and washed with water. The solid is air-dried, pulverized, and washed with acetonitrile. Upon drying, this crude product is treated with hot acetone whereby there is obtained 5,6,7,8-tetrahydro-4H-cyclohepta[b]thien-4-ylurea, m.p. 217° C. dec.

EXAMPLE 3

Preparation of 1-(methoxymethyl)-3-(5,6,7,8-tetrahydro-4H-cyclohepta[b]thien-4-yl)urea In 150 ml. of methanol is stirred 8.24 grams of 5,6,7,8-tetrahydro-4H-cyclohepta[b]thien-4-ylurea and 2.1 grams of sodium hydroxide pellets followed by 2.31 grams of paraformaldehyde in 50 ml. of methanol. The mixture is heated at reflux for 10 hours and cooled to afford crystals which are collected. The filtrate is evaporated to dryness and the residue is washed with water to afford more solid. Recrystallization of the combined fractions from acetone-hexane gives 1-(methoxymethyl)-3-(5,6,7,8-tetrahydro-4H-cyclohepta[b]thien-4-yl)urea, m.p. 197°–201° C. dec.

EXAMPLE 4

Preparation of 5,6,7,8-tetrahydro-4H-8-oxocyclohepta[b]thien-4-ylurea

In 375 ml. of 50% aqueous acetic acid is dissolved 6 grams of 5,6,7,8-tetrahydro-4H-cyclohepta[b]thien-4-ylurea, and 75 grams of ceric ammonium nitrate is added portionwise over a 10 minute period with stirring at 25°–35° C. The pale orange solution is stirred for another five minutes and 100 ml. of water is added. The solution is extracted twice with ethyl acetate (450 ml. and 350 ml.) and the combined extracts are washed with 100 ml. of water. The organic extract is evaporated to dryness in vacuo and the brown residue is recrystallized from methanol to afford 5,6,7,8-tetrahydro-4H-8-oxocyclohepta[b]thien-4-ylurea, m.p. 246°–248° C. dec.

EXAMPLE 5

Mouse Growth Regulant Tests

CFI female mice from Carworth Farms are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreaded controls are included in each test. Test data are provided in Table VI below wherein data are reported as percent weight gain over controls. Unless otherwise indicated in this table, all compounds tested were dl-racemic mixtures. The following is a description of the diet to which the growth promoting compounds were added.

DIET

| GUARANTEED ANALYSIS | |
|---|---|
| Crude protein not less than | 23.0% |
| Crude fat not less than | 4.5% |
| Crude fiber not more than | 6.0% |
| Ash not more than | 9.0% |

| INGREDIENTS |
|---|
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, chloine chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. |

TABLE VI

Effectiveness of 5,6,7,8-Tetrahydro-4H-cyclohepta[b]thien-4-ylureas as Animal Growth Promoting Agents Reported as Percent Weight Gain Over Controls Using Mice as the Test Animal

| Rate ppm in Diet | X | Y | $R_1$ | $R_3$ | $R_2$ | % Weight Gain Over Controls |
|---|---|---|---|---|---|---|
| 400 | O | CH$_2$— | H | H | H | 54 |
| 400 | O | CH$_2$— | H | H | —CH$_3$ | 41 |
| 400 | S | CH$_2$— | H | H | —C$_2$H$_5$ | 40 |
| 400 | O | CH$_2$— | H | H | —CH$_2$OCH$_3$ | 10 |
| 400 | O | C(=O)— | H | H | H | 68.8 |

EXAMPLE 6

Preparation of cis- and trans-5,6,7,8-tetrahydro-8-hydroxy-4 H-cyclohepta[b]thien-4-ylurea A sample of 1.72 g. of 5,6,7,8-tetrahydro-8-oxo-4H-cyclohepta[b]thien-4-ylurea is stirred in 120 ml. of absolute ethyl alcohol and 0.5 g. of sodium borohydride is added. After 5.5 hours, 50 ml. of water is added to the mixture and the mixture is evaporated to dryness in vacuo. Acetone is added to the residue and the mixture is evaporated to dryness. The residue is then extracted with 3×75 ml. portions of boiling acetone, the acetone solution being decanted each time. The combined acetone solutions are filtered and evaporated to dryness. The residue is then washed with diethyl ether and the insoluble solid (contains some gum) is crystallized from methyl alcohol/ethyl acetate to afford 0.148 g. of yellow solid. The mother liquor is evaporated to dryness and chromatographed on preparative thin-layer silica-gel chromatographic plates with 15 parts methanol/85 parts chloroform. A fraction melting at 171°–175° C. is then obtained after separation and recrystallization from methanol/ethyl acetate. This material analyzes acceptably (carbon, hydrogen and nitrogen) for the title compound and the infrared spectrum also supports the structure. A second fraction melting at 169°–172° C. is also obtained and its infrared spectrum is virtually identical with that of the above-mentioned fraction.

In the same manner, the compounds of formula XXI are prepared by replacing 5,6,7,8-tetrahydro-8-oxo-4H-cyclohepta[b]thien-4-yl-urea with compounds of formula XX wherein

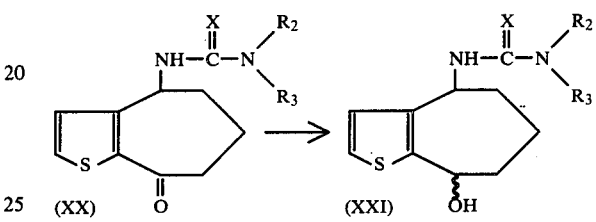

X, $R_2$ and $R_3$ are as defined in Table VII below:

TABLE VII

| X | $R_3$ | $R_2$ |
|---|---|---|
| O | n-butyl | H |
| O | H | n-octyl |
| O | H | methyl |
| S | H | ethyl |
| O | methyl | methyl |
| O | n-butyl | n-butyl |
| O | H | sec-butyl |
| S | H | sec-butyl |
| O | H | propargyl |
| O | H | alkyl |
| O | H | benzyl |
| O | H | methoxy |
| O | H | ethoxy |
| O | methyl | hydroxy |

EXAMPLE 7

Preparation of N-(5,6,7,8-tetrahydro-8-oxo-4H-cyclohepta[b]thien-4-yl)formamide.

In the manner described in Example 4, N-(5,6,7,8-tetrahydro-4H-cyclohepta[b]thien-4-yl)formamide is oxidized to afford N-(5,6,7,8-tetrahydro-8-oxo-4H-cyclohepta[b]thien-4-yl)formamide.

EXAMPLE 8

Preparation of 5,6,7,8-tetrahydro-8-oxo-4H-cyclohepta[b]thiophen-4-amine

In the manner described in Example 1, N-(5,6,7,8-tetrahydro-8-oxo-4H-cyclohepta[b]thien-4-yl)formamide is hydrolyzed to afford 5,6,7,8-tetrahydro-8-oxo-4H-cyclohepta[b]-thiophen-4-amine hydrochloride, which is treated with 10% aqueous sodium hydroxide solution to afford the title compound.

EXAMPLE 9

Preparation of 1-methyl-3-(5,6,7,8-tetrahydro-8-oxo-4H-cyclohepta[b]thien-4-yl)urea.

Stoichiometric quantities of 5,6,7,8-tetrahydro-8-oxo-4H-cyclohepta[b]thiophen-4-amine hydrochloride, methyl isocyanate, and triethylamine are allowed to react in dry methylene chloride to afford the title compound.

Similarly, replacement of methylisocyanate with the isocyanates or isothiocyanates set forth in Table VIII below afford the corresponding ureas of formula XXII.

TABLE VIII (XXII)

$$\underset{\substack{\| \\ O}}{\overset{\substack{X \\ \|}}{NH-C-NH-R_2}}$$

(structure of 5,6,7,8-tetrahydro-8-oxo-4H-cyclohepta[b]thien-4-yl)

| Isocyanate or Isothiocyanate | X | $R_2$ |
|---|---|---|
| CH₃NCS | S | methyl |
| C₂H₅NCO | O | ethyl |
| C₂H₅NCS | S | ethyl |
| 2-C₃H₇NCO | O | iso-propyl |
| 2-C₄H₉NCO | O | sec-butyl |
| 2-C₄H₉NCS | S | sec-butyl |
| C₆H₅CH₂NCO | O | benzyl |
| n-C₈H₁₇NCO | O | n-octyl |
| Cl₃C—C(=O)—NCO | O | trichloroacetyl |
| C₆H₅—C(=O)—NCO | O | benzoyl |

EXAMPLE 10

Preparation of 1-(2-propynyl)-3-(5,6,7,8-tetrahydro-4H-cyclohepta[b]-4-yl)urea.

An equivalent amount of 5,6,7,8-4H-cyclohepta[b]thiophen-4-amine hydrochloride is converted to the free amine with aqueous 10% sodium hydroxide, extracted with methylene chloride, and the solution is dried over MgSO₄, filtered, and added to carbonyl diimidazole (11 grams) in 50 ml. of methylene chloride. After an hour of stirring, 3.74 g. of propargylamine is added in 50 ml. of methylene chloride. After 3 hours, the crude title compound is collected by filtration.

Similarly, the amines R₂R₃NH set forth in Table IX below are substituted for propargylamine in the above procedure to afford the corresponding ureas of formula XXIII.

TABLE IX

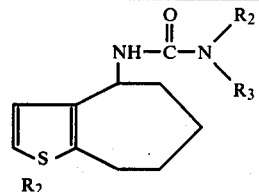

(XXIII)

| $R_2$ | $R_3$ |
|---|---|
| methyl | methyl |
| allyl | H |
| methoxy | H |

TABLE IX-continued

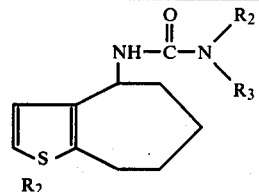

(XXIII)

| $R_2$ | $R_3$ |
|---|---|
| methoxy | methyl |
| hydroxy | H |
| hydroxy | methyl |
| n-butyl | n-butyl |
| n-octyl | H |
| ethoxy | H |
| n-butoxy | H |
| phenoxy | H |

EXAMPLE 11

Preparation of 1-(2-propynyl)-3-(5,6,7,8-tetrahydro-8-oxo-4H-cyclohepta[b]thien-4-yl)urea.

A sample of 11 grams of carbonyl diimidazole in 50 ml. of methylene chloride is stirred and an equivalent amount of 5,6,7,8-tetrahydro-8-oxo-4H-cyclohepta[b]thiophen-4-amine in 50 ml. of methylene chloride is added. After one hour, 3.74 grams of propargylamine in 50 ml. of methylene chloride is added. The mixture is stirred at room temperature for 3 hours and the title compound is collected by filtration.

Similarly, substitution of the amines R₂R₃NH set forth in Table X below for propargylamine affords the ureas of formula (XXIV).

TABLE X

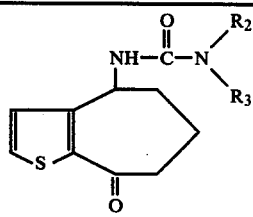

(XXIV)

| $R_2$ | $R_3$ |
|---|---|
| methyl | methyl |
| allyl | H |
| methoxy | H |
| methoxy | methyl |
| hydroxy | methyl |
| n-butyl | n-butyl |
| n-octyl | H |
| ethoxy | H |
| n-butoxy | H |
| iso-propyl | H |
| phenoxy | H |

EXAMPLE 12

Preparation of 1-methyl-b 1-(5,6,7,8-tetrahydro-4H-cyclohepta[b]thien-4-yl)urea 5,6,7,8-Tetrahydro-4H-cyclohepta[b]thiophen-4-one is converted to N-methyl-N-(5,6,7,8-tetrahydro-4H-cyclohepta[b]thien-4-yl)formamide by substituting methylformamide for formamide in the method of Kloetzel et al., Journal of Organic Chemistry 18, 1511 (1953). The formamide is then hydrolyzed by the method of Example 1 and the amine hydrochloride is reacted with potassium cyanate by the method outlined in Example 2 to afford the title compound.

The amine hydrochloride is also allowed to react with equivalent amounts of methyl isocyanate and triethylamine in methylene chloride to afford 1,3-dimethyl-3-(5,6,7,8-tetrahydro-4H-cyclohepta[b]thien-4-yl)urea.

EXAMPLE 13

Preparation of 1-isopropyl-3-(5,6,7,8-tetrahydro-4H-cyclohepta[b]thien-4-yl)urea.

In dry tetrahydrofuran, stoichiometric quantities of isopropyl isocyanate, 5,6,7,8-tetrahydro-4H-cyclohepta[b]thiophen-4-amine hydrochloride, and triethylamine are stirred at room temperature for 2 hours and then heated at reflux for half an hour. The title product is then collected and washed with water.

Similarly, replacement of isopropyl isocyanate with the isocyanates or isothiocyanates set forth in Table XI below afford the corresponding ureas and thioureas of formula (XXV).

TABLE XI

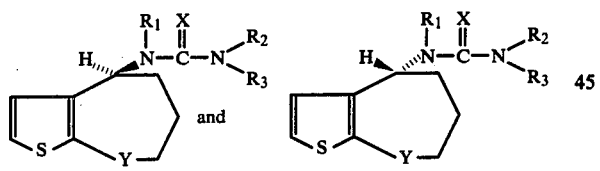

(XXV)

| Isocyanate or Isothiocyanate | X | R$_2$ |
|---|---|---|
| n-C$_4$H$_9$NCS | S | n-butyl |
| 2-C$_4$H$_9$NCO | O | sec-butyl |
| Cl$_3$C—C(O)—NCO | O | trichloroacetyl |
| C$_6$H$_5$—C(O)—NCO | O | benzoyl |
| C$_6$H$_5$CH$_2$NCO | O | benzyl |
| n-C$_8$H$_{17}$NCO | O | n-octyl |

I claim:

1. A compound selected from the group consisting of those of the formulae:

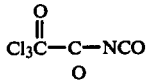 and 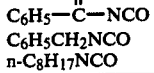

wherein X is oxygen or sulfur; Y is a divalent radical selected from the group consisting of those of the formulae:

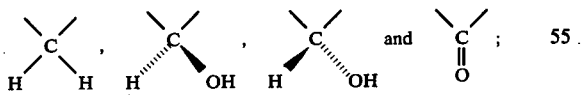

R$_1$ is hydrogen or alkyl C$_1$–C$_4$; R$_3$ is selected from the group consisting of hydrogen, alkyl C$_1$–C$_4$, cycloalkyl C$_3$–C$_6$, allyl, 2-propynyl, benzyl and β-phenethyl; R$_2$ is selected from the group consisting of the substituents listed in the following table:

hydrogen
alkyl C$_1$—C$_{12}$
cycloalky; C$_3$—C$_6$
allyl
methallyl
2-butenyl
2-propynyl
hydroxy
alkoxy C$_1$—C$_6$
allyloxy
methallyloxy
2-butenyloxy
methoxymethyl
phenoxy
—CH$_2$—CH$_2$—OH
—CH$_2$—CH$_2$—O—CH$_3$
—CH$_2$—CH$_2$—S—CH$_3$
—CH$_2$—CH(OR)$_2$
—CH$_2$—CF$_3$
—CH$_2$—CN
—CH$_2$—CO$_2$R
—NH—CO$_2$R
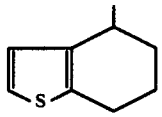

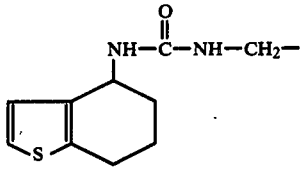

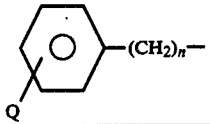

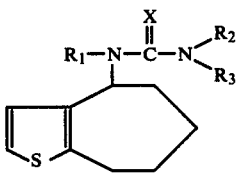

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
| 3- or 4-methoxy | 4-chloro | |
| 4-ethoxy | 4-methoxy | |
| 4-chloro | | |
| 4-butoxy | | |
| 4-methylthio | | |
| 2,4-dimethyl | | |
| 2,4-dichloro | | |
| 4-nitro | | |

2. The compound according to claim 1 selected from the group consisting of the dextrorotatory enantiomorph, the levorotatory enantiomorph, and the racemic mixture thereof of a compound of the formula:

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and β-phenethyl; $R_2$ is selected from the group consisting of the substituents listed in the following table:

| |
|---|
| hydrogen |
| alkyl $C_1$—$C_{12}$ |
| cycloalky; $C_3$—$C_6$ |
| allyl |
| methallyl |
| 2-butenyl |
| 2-propynyl |
| hydroxy |
| alkoxy $C_1$—$C_6$ |
| allyloxy |
| methallyloxy |
| 2-butenyloxy |
| methoxymethyl |
| phenoxy |
| —$CH_2$—$CH_2$—OH |
| —$CH_2$—$CH_2$—O—$CH_3$ |
| —$CH_2$—$CH_2$—S—$CH_3$ |
| —$CH_2$—$CH(OR)_2$ |
| —$CH_2$—$CF_3$ |
| —$CH_2$—CN |
| —$CH_2$—$CO_2R$ |
| —NH—$CO_2R$ |
| $\begin{matrix}O\\\|\\-C-R\end{matrix}$ |
| $\begin{matrix}O\\\|\\-C-CCl_3\end{matrix}$ |

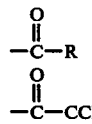

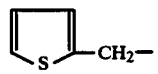

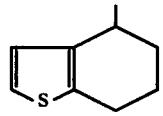

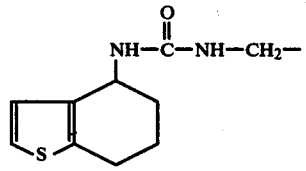

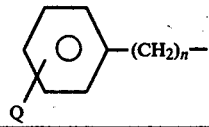

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy | | |
| 4-chloro | | |
| 4-butoxy | | |
| 4-methylthio | | |
| 2,4-dimethyl | | |
| 2,4-dichloro | | |
| 4-nitro | | |

3. The racemic mixture according to claim 2 wherein X is oxygen and $R_1$, $R_2$ and $R_3$ are hydrogen; dl-5,6,7,8-tetrahydro-4H-cyclohepta[b]thien-4-ylurea.

4. The dextrorotatory enantiomorph according to claim 2 wherein X is oxygen and $R_1$, $R_2$ and $R_3$ are hydrogen; d-5,6,7,8-tetrahydro-4H-cyclohepta[b]thien-4-ylurea.

5. The levorotatory enantiomorph according to claim 2 wherein X is oxygen and $R_1$, $R_2$ and $R_3$ are hydrogen, 1-5,6,7,8-tetrahydro-4H-cyclohepta[b]-thien-4-ylurea.

6. The racemic mixture according to claim 2 wherein X is oxygen, $R_1$ and $R_2$ are hydrogen, $R_3$ is methyl, dl-1-methyl-3-(5,6,7,8-tetrahydro-4H-cyclohepta[b]thien-4-yl)urea.

7. The racemic mixture according to claim 2 wherein X is sulfur, $R_1$ and $R_2$ are hydrogen, and $R_3$ is ethyl; dl-1-ethyl-3-(5,6,7,8-tetrahydro-4H-cyclohepta[b]thien-4-yl)-2-thiourea.

8. The racemic mixture according to claim 2 wherein X is oxygen, $R_1$ is hydrogen; $R_2$ is methoxymethyl, and $R_3$ is hydrogen; dl-1 methoxymethyl-3-(5,6,7,8-tetrahydro-4H-cyclohepta[b]thien-4-yl)urea.

9. The compound according to claim 1 selected from the group consisting of the dextrorotatory enantiomorph, the levorotatory enantiomorph, and the racemic mixture thereof of a compound of the formula:

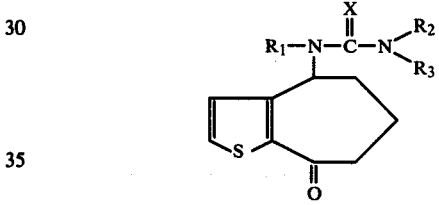

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and β-phenethyl; $R_2$ is selected from the group consisting of the substituents listed in the following table:

| |
|---|
| hydrogen |
| alkyl $C_1$—$C_{12}$ |
| cycloalky; $C_3$—$C_6$ |
| allyl |
| methallyl |
| 2-butenyl |
| 2-propynyl |
| hydroxy |
| alkoxy $C_1$—$C_6$ |
| allyloxy |
| methallyloxy |
| 2-butenyloxy |
| methoxymethyl |
| phenoxy |
| —$CH_2$—$CH_2$—OH |
| —$CH_2$—$CH_2$—O—$CH_3$ |
| —$CH_2$—$CH_2$—S—$CH_3$ |
| —$CH_2$—$CH(OR)_2$ |
| —$CH_2$—$CF_3$ |
| —$CH_2$—CN |
| —$CH_2$—$CO_2R$ |
| —NH—$CO_2R$ |
| $\begin{matrix}O\\\|\\-C-R\end{matrix}$ |
| $\begin{matrix}O\\\|\\-C-CCl_3\end{matrix}$ |

-continued

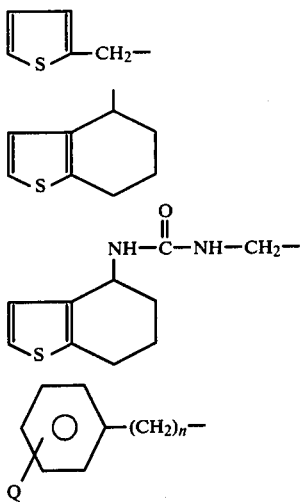

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

10. The racemic mixture according to claim 9 wherein X is oxygen and $R_1$, $R_2$ and $R_3$ are hydrogen; dl-5,6,7,8-tetrahydro-8-oxo-4H-cyclohepta[b]thien-4-ylurea.

11. The dextrorotatory enantiomorph according to claim 9 wheren X is oxygen and $R_1$, $R_2$ and $R_3$ are hydrogen; d-5,6,7,8-tetrahydro-8-oxo-4H-cyclohepta[b]thien-4-ylurea.

12. The levorotatory enantiomorph according to claim 9 wherein X is oxygen and $R_1$, $R_2$ and $R_3$ are hydrogen; 1-5,6,7,8-tetrahydro-8-oxo-4H-cyclohepta[b]thien-4-ylurea.

13. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

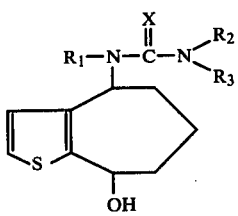

wherein X is oxygen or sulfur; $R_1$ is hydrogen or alkyl $C_1$–$C_4$; $R_3$ is selected from the group consisting of hydrogen, alkyl $C_1$–$C_4$, cycloalkyl $C_3$–$C_6$, allyl, 2-propynyl, benzyl and β-phenethyl; $R_2$ is selected from the group consisting of the substituents listed in the following table:

hydrogen
alkyl $C_1$—$C_{12}$
cycloalky; $C_3$—$C_6$
allyl
methallyl
2-butenyl
2-propynyl
hydroxy
alkoxy $C_1$—$C_6$
allyloxy
methallyloxy
2-butenyloxy
methoxymethyl
phenoxy
—$CH_2$—$CH_2$—OH
—$CH_2$—$CH_2$—O—$CH_3$
—$CH_2$—$CH_2$—S—$CH_3$
—$CH_2$—$CH(OR)_2$
—$CH_2$—$CF_3$
—$CH_2$—CN
—$CH_2$—$CO_2R$
—NH—$CO_2R$ $$-\overset{O}{\underset{\|}{C}}-R$$

$$-\overset{O}{\underset{\|}{C}}-CCl_3$$

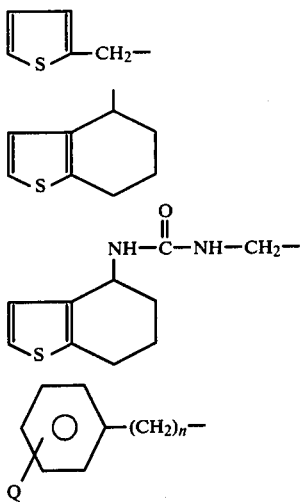

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

14. The cis-racemic mixture according to claim 13 wherein X is oxygen and $R_1$, $R_2$ and $R_3$ are hydrogen; dl-cis-5,6,7,8-tetrahydro-8-hydroxy-4H-cyclohepta[b]-thien-4-yl-urea.

15. The trans-racemic mixture according to claim 13 wherein X is oxygen and $R_1$, $R_2$ and $R_3$ are hydrogen; dl-trans-5,6,7,8-tetrahydro-8-hydroxy-4H-cyclohepta[b]thien-4-ylurea.

16. The cis-dextrorotatory enantiomorph according to claim 13 wherein X is oxygen and $R_1$, $R_2$ and $R_3$ are hydrogen; d-cis-5,6,7,8-tetrahydro-8-hydroxy-4H-cyclohepta[b]thien-4-ylurea.

17. The cis-levorotatory enantiomorph according to claim 13 wherein X is oxygen and $R_1$, $R_2$ and $R_3$ are hydrogen; l-cis-5,6,7,8-tetrahydro-8-hydroxy-4H-cyclohepta[b]thien-4-ylurea.

18. The trans-dextrorotatory enantiomorph according to claim 13 wherein X is oxygen and $R_1$, $R_2$ and $R_3$ are hydrogen; d-trans-5,6,7,8-tetrahydro-8-hydroxy-4H-cyclohepta[b]thien-4-ylurea.

19. The trans-levorotatory enantiomorph according to claim 13 wherein X is oxygen and $R_1$, $R_2$ and $R_3$ are hydrogen; l-trans-5,6,7,8-tetrahydro-8-hydroxy-4H-cyclohepta[b]-thien-4-ylurea.

20. The compound according to claim 1 selected from the group consisting of the dextrorotatory enantiomorph, the levorotatory enantiomorph, and the racemic mixture thereof of a compound of the formula:

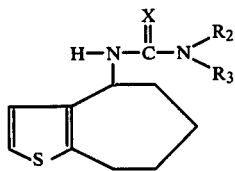

wherein X is oxygen or sulfur; $R_2$ is selected from the group consisting of hydrogen, alkyl $C_1$–$C_8$, allyl, alkoxy $C_1$–$C_4$, 2-propynyl, hydroxy and methoxymethyl; and $R_3$ is hydrogen or alkyl $C_1$–$C_4$.

21. The compound according to claim 1 selected from the group consisting of the dextrorotatory enantiomorph, the levorotatory enantiomorph, and the racemic mixture thereof of a compound of the formula:

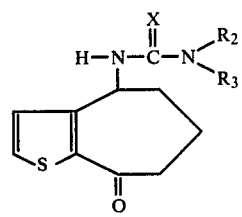

wherein X is oxygen or sulfur; $R_2$ is selected from the group consisting of hydrogen, alkyl $C_1$–$C_8$, allyl, alkoxy $C_1$–$C_4$, 2-propynyl, hydroxy and methoxymethyl; and $R_3$ is hydrogen or alkyl $C_1$–$C_4$.

22. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

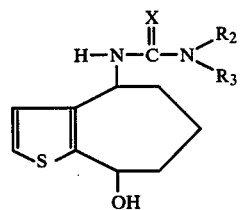

wherein X is oxygen or sulfur; $R_2$ is selected from the group consisting of hydrogen, alkyl $C_1$–$C_8$, allyl, alkoxy $C_1$–$C_4$, 2-propynyl, hydroxy and methoxymethyl; and $R_3$ is hydrogen or alkyl $C_1$–$C_4$.

* * * * *